(12) United States Patent  (10) Patent No.: US 7,105,172 B1
Bolla  (45) Date of Patent: Sep. 12, 2006

(54) TREATMENT OF ROSACEA

(76) Inventor: John D. Bolla, 35 Carlson La., Palm Coast, FL (US) 32137

( * ) Notice: Subject to any disclaimer, the term of this patent is extended or adjusted under 35 U.S.C. 154(b) by 0 days.

(21) Appl. No.: 09/715,644

(22) Filed: Nov. 17, 2000

Related U.S. Application Data

(60) Provisional application No. 60/166,235, filed on Nov. 18, 1999.

(51) Int. Cl.
  A61K 9/00 (2006.01)
  A61K 9/127 (2006.01)
  A61K 9/48 (2006.01)
  A61K 31/74 (2006.01)
  A01N 43/64 (2006.01)

(52) U.S. Cl. .............. 424/400; 424/450; 424/451; 424/464; 424/78.05; 514/381

(58) Field of Classification Search ............ 424/78.05, 424/400, 401, 450, 9.2, 449, 78.02, 78.03; 514/863, 870, 871, 886, 887, 159, 947, 944
See application file for complete search history.

(56) References Cited

U.S. PATENT DOCUMENTS

| 4,944,949 | A | * | 7/1990 | Story et al. | 424/451 |
| 4,954,487 | A | * | 9/1990 | Cooper et al. | 514/159 |
| 5,212,182 | A |  | 5/1993 | Musser et al. |  |
| 5,409,899 | A |  | 4/1995 | Fauchere et al. |  |
| 5,416,191 | A |  | 5/1995 | Cheronis et al. |  |
| 5,464,820 | A | * | 11/1995 | Burton et al. | 514/16 |
| 5,563,162 | A |  | 10/1996 | Oku et al. |  |
| 5,569,651 | A | * | 10/1996 | Garrison et al. | 514/159 |
| 5,574,042 | A |  | 11/1996 | Oku et al. |  |
| 5,597,803 | A |  | 1/1997 | Breipohl et al. |  |
| 5,610,140 | A |  | 3/1997 | Goodfellow et al. |  |
| 5,620,958 | A |  | 4/1997 | Cheronis et al. |  |
| 5,635,593 | A |  | 6/1997 | Cheronis et al. |  |
| 5,700,779 | A |  | 12/1997 | Goodfellow et al. |  |
| 5,741,794 | A | * | 4/1998 | Bowles et al. | 514/261 |

(Continued)

FOREIGN PATENT DOCUMENTS

AU    660809    12/1993

(Continued)

OTHER PUBLICATIONS

Guarrera et al, Flushing in Rosacea: A Possible Mechanism, Archives Dermatologicla Research, 1982; 272 (3-4):311-6.*

(Continued)

Primary Examiner—Sreeni Padmanabhan
Assistant Examiner—S. Gollamudi
(74) Attorney, Agent, or Firm—Kristina Bieker-Brady; Clark & Elbing LLP

(57) ABSTRACT

Disclosed herein are methods for the treatment or prevention of rosacea in a patient, including administering a compound that inhibits one or more components of the bradykinin activation pathway in an amount sufficient to reduce or prevent one or more symptoms of rosacea.

9 Claims, 1 Drawing Sheet

U.S. PATENT DOCUMENTS

| | | | |
|---|---|---|---|
| 5,750,506 A | | 5/1998 | Goodfellow et al. |
| 5,750,699 A | | 5/1998 | Oku et al. |
| 5,795,574 A | * | 8/1998 | Breton et al. ............. 424/195.1 |
| 5,834,431 A | | 11/1998 | Stewart et al. |
| 5,837,270 A | * | 11/1998 | Burgess ...................... 424/401 |
| 5,843,900 A | | 12/1998 | Cheronis et al. |
| 5,849,312 A | * | 12/1998 | Breton et al. ................ 424/401 |
| 5,849,863 A | | 12/1998 | Stewart et al. |
| 5,863,899 A | | 1/1999 | Cheronis et al. |
| 5,897,880 A | * | 4/1999 | Drizen et al. ................ 424/488 |
| 5,968,951 A | | 10/1999 | Dodey et al. |
| 5,972,993 A | * | 10/1999 | Ptchelintsev ................ 514/449 |
| 6,017,932 A | * | 1/2000 | Singh et al. ................. 514/321 |
| 6,057,347 A | * | 5/2000 | Garvey et al. ............... 514/364 |
| 6,060,061 A | * | 5/2000 | Breton et al. ................ 424/745 |
| 6,071,955 A | * | 6/2000 | Elias et al. .................. 514/475 |
| 6,080,758 A | | 6/2000 | Dodey et al. |
| 6,150,403 A | * | 11/2000 | Biedermann et al. ........ 514/460 |
| 6,174,878 B1 | * | 1/2001 | Gamache et al. ...... 514/211.12 |
| 2003/0191098 A1 | * | 10/2003 | D'Amato .................... 514/171 |

FOREIGN PATENT DOCUMENTS

| | | |
|---|---|---|
| EP | 0 548 825 B1 | 6/1993 |
| EP | 0 552 106 B1 | 7/1993 |
| EP | 0 564 972 A3 | 10/1993 |
| EP | 0 578 521 A1 | 1/1994 |
| EP | 0 596 406 B1 | 5/1994 |
| EP | 0 622 361 A1 | 11/1994 |
| FR | 2768622 * | 1/2002 |
| WO | WO 93/11789 | 6/1993 |
| WO | WO 96/13485 | 5/1996 |
| WO | WO 96/40639 | 12/1996 |
| WO | WO 97/07115 | 2/1997 |
| WO | WO 97/11069 | 3/1997 |

OTHER PUBLICATIONS

Bhoola et al., "Bioregulation of Kinins: Kallikreins, Kininogens, and Kininases," *Pharmacological Reviews*, 44:1-80 (1992).

Fisher et al., "Cellular, Immunologic and Biochemical Characterization of Topical Retinoic Acid-Treated Human Skin," *J. Invest. Dermatol.*, 96:699-707 (1991).

Regoli et al., "Pharmacology of Bradykinin and Related Kinins," *Pharmacological Reviews*, 32:1-46 (1980).

Siragy et al., "Protective Role of the Angiotensin $AT_2$ Receptor in a Renal Wrap Hypertension Model," 33:1237-1242 (1999).

Starr et al., "Bradykinin and Oedema Formation in Heated Paws of Rats," *Br. J. Pharmac. Chemother.*, 31:178-187 (1967).

Guarrera et al., "Flushing In Rosacea: A Possible Mechanism," *Arch. Dermatol. Res.* 272:311-316 (1982).

Juhlin, "Late-phase Cutaneous Reactions To Platelet Activating Factor And Kallikrein In Urticaria," *Clinical and Experimental Allergy*, Supplemental 4, 90:9-10 (1990).

Michaëlsson, "Effects of Antihistamines, Acetylsalicylic Acid and Prednisone on Cutaneous Reactions to Kallikrein and Prostaglandin $E_1$," *Acta Dermatovener* 50:31-36 (1970).

Starr et al., "Oculocutaneous Aspects of Rosacea," *Proc. roy. Soc. Med.* 62:9-11 (1969).

Thomas et al., "Prostaglandins, Kinin and Inflammation In the Rat," *Br. J. Pharmac.* 50:231-235 (1974).

* cited by examiner

TREATMENT OF ROSACEA

CROSS REFERENCE TO RELATED APPLICATIONS

This application claims priority from U.S. provisional application U.S. Ser. No. 60/166,235, filed Nov. 18, 1999.

BACKGROUND OF THE INVENTION

The invention described herein relates to methods for treating rosacea.

Rosacea is a chronic skin condition characterized by recurrent episodes of flushing, erythema, vasodilation, telangiectasia, edema, papules, pustules, hyperplasia, fibroplasia, itching, burning, pain, and skin tightness. Symptoms of rosacea are exacerbated by sun exposure, hot weather, immersion in hot water, high humidity, sweating, exercise, emotional stress, and spicy food. The skin condition usually begins between the ages of 30 to 50 and occurs more frequently in women than men.

The etiology of rosacea is not well understood, but it has been presumed to be caused by an as yet unidentified infectious agent. Unfortunately, antibiotic administration yields only marginal improvement (see, e.g., Dahl et al., Archives of Dermatology 134: 679–683, 1998; Bamford et al., Archives of Dermatology 135: 659–663, 1999). Therefore, there is a clear need for the identification of new targets in the pathology of rosacea, and the development of drugs that affect these new targets.

Bradykinins are autocoids, that is, they are hormones that are synthesized locally and act locally. This local effect is due to the short half-life (less than 30 seconds) of bradykinins and their almost complete destruction in the first pass through the pulmonary circulation (Ferreira and Vane, Chemotherap. 30: 317, 1967).

The major effects induced by bradykinins are vasodilation, increased vascular permeability, and inflammation. The inflammatory process involves the infiltration of neutrophils, macrophages, lymphocytes, mast cells, and other lamina proprira cells, including fibroblasts, to the site of inflammation. These inflammatory cells then function to synthesize and release several arachidonic acid-related mediators of inflammation, such as prostaglandins, leukotrienes, and thromboxanes. Bradykinins also lower blood pressure, participate in blood clotting and complement reactions, and cause pain.

The group of bradykinins, which includes Lys-bradykinin (kallidin) and Met-Lys bradykinin, as well as bradykinin, are produced by kallikrein cleavage of kininogen. Kininogen is a hepatic-derived protein which circulates in the blood in a low molecular weight form and a high molecular weight form. Kallikreins can be divided into two groups of serine proteases: tissue kallikreins (EC number 3.4.21.35) and plasma kallikrein (EC number 3.4.21.34). Tissue kallikreins are relatively specific for cleavage of the low molecular weight form of kininogen; plasma kallikrein has greater specificity for the high molecular weight form.

Plasma kallikrein has a molecular weight of about 100 kD, circulates in the blood in a precursor form called prekallikrein, and is principally involved in the activation of the blood clotting and compliment enzyme cascades. Tissue kallikreins, otherwise known as glandular or organ kallikreins, are glycoproteins with a molecular weight ranging from 27–40 kD. They have been isolated from various tissues and body fluids including saliva, intestine, lung, brain, plasma, and the sweat glands of the skin. Their substrates include procollagenase, kininogen, proinsulin, prorenin, BAM 22P atrial natriuretic factor, low density lipoprotein, atriopeptigen, and tissue plasminogen activator.

Angiotensin II is an important factor in blood pressure regulation and in the pathophysiology of renovascular hypertension. Its precursor, angiotensin I, is produced and released into the circulation in response to renin. Angiotensin converting enzyme (ACE) converts angiotensin I into angiotensin II, which mediates vasoconstriction via stimulation of the AT1 receptor and the production of bradykinin via stimulation of the AT2 receptor (Siragy and Carey, Hypertension 33: 1214–1217, 1999; Gohlke and Unger, Hypertension 31: 349–355, 1998).

SUMMARY OF THE INVENTION

The present invention results from my discovery of a causal link between the activation of the bradykinin pathway and rosacea. Accordingly, the invention features a method of treating or preventing rosacea by administering a compound that inhibits a component or components of the bradykinin activation pathway.

The compounds described herein for treating rosacea preferably inhibit bradykinin activity, kallikrein activity, angiotensin II activation of the AT2 receptor, or an enzyme in the arachidonic acid metabolic pathway. More preferably, the bradykinin inhibitor is specific for the BK2 receptor, the kallikrein inhibitor is specific for tissue kallikreins, the AT2 inhibitor is specific for the AT2 receptor, and the inhibitor of the arachidonic acid metabolic pathway is specific for the prostaglandin arm of the pathway. The compounds can be administered systemically or topically. For topical administration, the compound may be included in a liposomal formulation.

The method includes administering a compound to a patient in an amount sufficient to reduce or prevent one or more symptoms of rosacea. The symptoms of rosacea are mediated by activation of the pathway, and can be caused by inflammation, vasodilation, or increased vascular permeability in the skin. Examples of symptoms of rosacea include any of the following appearing in or associated with the skin: flushing, erythema, vasodilation, telangiectasia, edema, papules, pustules, hyperplasia, fibroplasia, itching, burning, pain, and tightness of the skin. The patient may also suffer from elevated levels of angiotensin II.

The invention also includes a method of assessing whether an inhibitor of the bradykinin activation pathway is an effective compound for treating or preventing rosacea. The method involves contacting the compound with skin and measuring whether the compound significantly reduces bradykinin production in the skin or a bradykinin activation pathway-related change in the skin.

By "a kallikrein" is meant a tissue kallikrein or plasma kallikrein.

By "a bradykinin" is meant bradykinin, Lys-bradykinin (kallidin), or Met-Lys bradykinin.

By "an enzyme in the arachidonic acid metabolic pathway" is meant an enzyme, such as cyclooxygenase, lipoxygenase, or prostaglandin synthetase, that plays a role in converting arachidonic acid to various products such as prostaglandins, leukotrienes, and thromboxanes.

By "a component of the bradykinin activation pathway" is meant the following: a kallikrein or angiotensin II, which plays a role in increasing bradykinin production; a bradykinin; or an enzyme in the arachidonic acid metabolic pathway; wherein the component causes or mediates an effect of bradykinin activation that causes a symptom of rosacea.

By "an inhibitor of the bradykinin activation pathway" is meant a compound that inhibits a component of the bradykinin activation pathway, such that the activation is reduced. This inhibition results in a reduced occurrence of a symptom of rosacea, or a reduction in a bradykinin activation pathway-related change in the skin. The inhibitor either inhibits or antagonizes the enzymatic or hormonal activity of the component or reduces the protein level of the component.

By "a symptom of rosacea" is meant any of the following appearing in the skin or associated with the skin: flushing, erythema, vasodilation, telangiectasia, edema, papules, pustules, hyperplasia, fibroplasia, itching, burning, pain, and skin tightness.

By "treating or preventing rosacea" is meant producing a detectable reduction in a symptom of rosacea, or preventing the occurrence or exacerbation of a symptom under conditions known to induce such symptoms, such as sun exposure, heat humidity, exercise, emotional stress, or after ingestion of spicy food. A reduction in a symptom of rosacea can be assessed, for example, using the Duluth Rosacea Scoring Instrument (Dahl et al., Arch. Dermatology 134: 679–683, 1998).

By "a bradykinin activation pathway-related change in the skin" is meant a change mediated by bradykinin activation, for example, inflammation, infiltration of inflammatory cells, vasodilation, increased vascular permeability, increased oxygen free radicals, increased nitric oxide, increased matrix metalloproteases (MMPs), or increased deposition of elastin material.

By "a kallikrein inhibitor" is meant any compound which causes a reduction of kallikrein enzymatic activity or protein level, and includes, but is not limited to, serpin, C1 inhibitor, α2 macroglobulin, antithrombin-III, ecotin, broad spectrum Kunitz-type serine protease inhibitors (such as aprotinin and its variants), an antibody to a kallikrein, diisopropylfluorophosphate, pefablock (Interchim), and other exemplary inhibitors listed in U.S. Pat. No. 5,786,328, U.S. Pat. No. 5,770,568, or U.S. Pat. No. 5,464,820.

By "an angiotensin II inhibitor" is meant any drug which causes a reduction in the activity or level of angiotensin II such that there is reduced activation of the AT2 receptor. Preferred inhibitors are either specific for the AT2 receptor, such as PD 123319 (Siragy and Carey, supra), or are balanced antagonists which block both the AT1 and AT2 receptors.

By a "bradykinin inhibitor" is meant a compound that reduces the activity or level of the autocoid. A preferred inhibitor is CP0597 (Cortech). Other exemplary inhibitors include, but are not limited to, those listed in U.S. Pat. No. 5,700,779; U.S. Pat. No. 5,750,506; U.S. Pat. No. 5,610,140; U.S. Pat. No. 5,863,899; U.S. Pat. No. 5,849,863; U.S. Pat. No. 5,843,900; U.S. Pat. No. 5,834,431, U.S. Pat. No. 5,635,593; U.S. Pat. No. 5,416,191; U.S. Pat. No. 5,620,958; U.S. Pat. No. 5,563,162; U.S. Pat. No. 5,750,669; U.S. Pat. No. 5,574,042; U.S. Pat. No. 4,801,613, U.S. Pat. No. 5,578,601, U.S. Pat. No. 4,693,993, WO 96/13485; WO 96/40639; WO 97/07115; WO 97/11069; EP 773,932 A1; EP 596,406 A1; EP 596,406 B1; EP 787,131 A1; EP 861,243 A1; EP 807,105 A1; EP 622,361 A1; and the indirect bradykinin inhibitors listed in U.S. Pat. No. 4,801,613. Preferred inhibitors are specific for the BK2 receptor, such as CP0597. Specifically excluded are icatibant and the compounds listed in U.S. Pat. No. 5,849,312, U.S. Pat. No. 5,212,182, EP 578,521, EP 564,972, EP 548,825, EP 552, 106, FR 2,686,343, and WO 93/11789.

By "an inhibitor of the arachidonic acid metabolic pathway" is meant a compound that reduces the activity or the level of cyclooxygenase, lipoxygenase, prostaglandin synthetase, or another enzyme that plays a role in converting arachidonic acid to its various metabolic products. Examples of such inhibitors include, but are not limited to, nonsteroidal anti-inflammatory drugs, salicylates, and cyclooxygenase inhibitors, such as rofecoxib and celecoxib.

By "a nonsteroidal anti-inflammatory drug (NSAID)" is meant a compound that prevents or reduces inflammation. Preferred NSAIDs include, but are not limited to, naproxen, nabumetone, diclofenac, sulindac, oxaprosin, diflunisal, bromfenac, aspirin, piroxicam, indomethacin, etodolac, ibuprofen, fenoprofen, flurbiprofen, ketorolac, nimesulide, NS-398, ketoprofen, trisalicylates, acetominophen, oxaprosin, salsalate, rofecoxib, and celecoxib.

The present invention has the advantage of providing novel targets to regulate in the treatment of rosacea and to provide treatment alternatives to antibiotics. The antibiotics may have limited efficacy and cause adverse effects such as gastrointestinal intolerance, photosensitivity, the development of antibiotic-resistant infections, and yeast infections.

Other features and advantages of the invention will be apparent from the following detailed description, and from the claims.

BRIEF DESCRIPTION OF THE FIGURE

FIG. 1 also points out the components of the bradykinin-related pathways that are inhibited to treat or prevent symptoms of rosacea (see stars).

DETAILED DESCRIPTION

Figure 1:
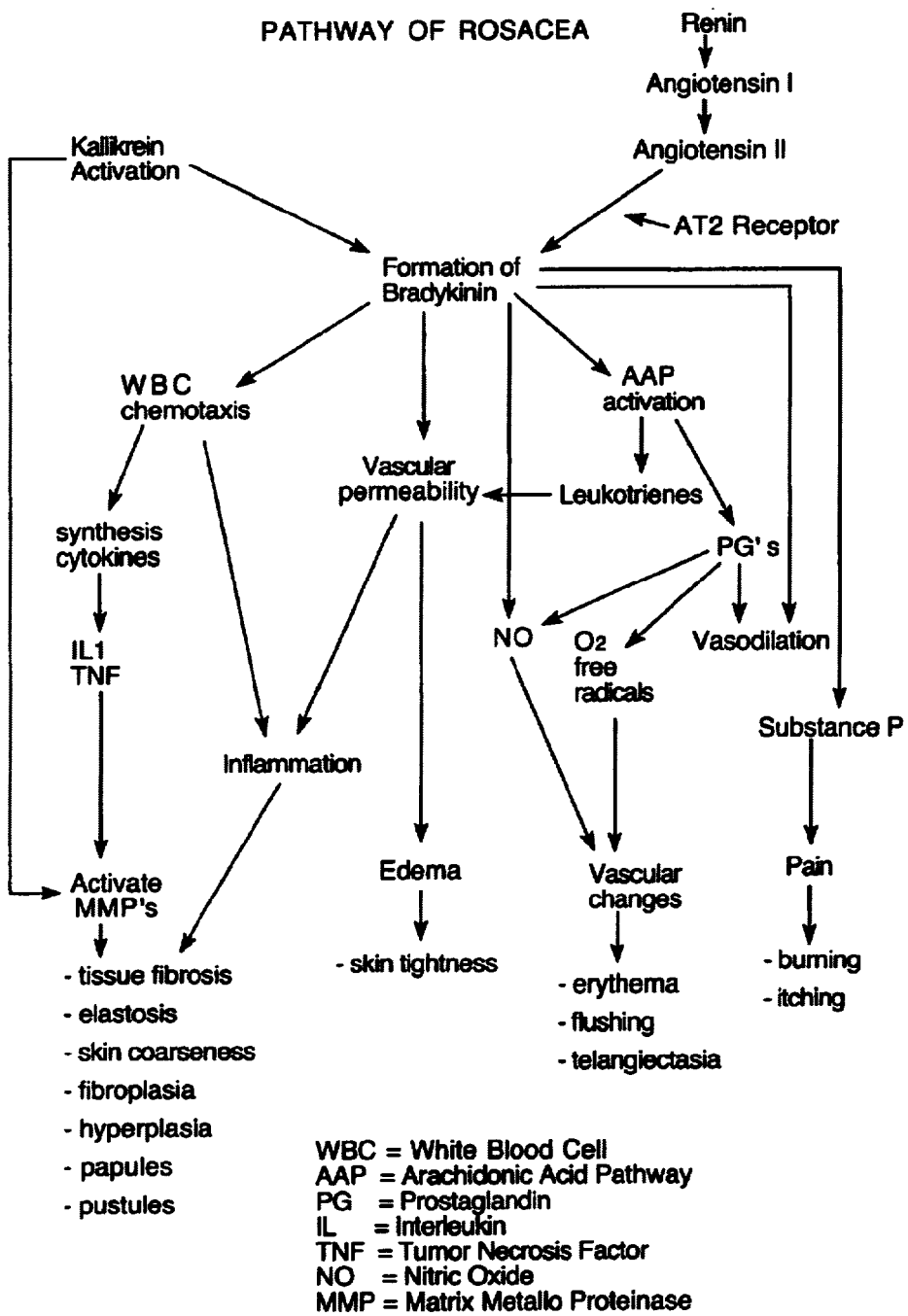
FIG. 1 is a diagram which demonstrates the causal connection between the increased production of bradykinin in the skin and symptoms of rosacea. The dermal bradykinin increase can result from activation of the kallikrein-kinin pathway or from increased angiotensin II stimulation of the AT2 receptor.

The present invention arises from my discovery of a causal connection between the local activation of bradykinin in the skin and the occurrence of symptoms of rosacea.

Accordingly, the present invention features a method of treating or preventing a symptom of rosacea by administering to a patient a compound that inhibits a component of the bradykinin activation pathway such that the effect of bradykinin is reduced.

The Bradykinin Activation Pathway is a Novel Mediator of Rosacea: A Rationale for Treatment I have found that the activation of the bradykinin pathway causes symptoms of rosacea by increasing inflammation, vasodilation, and vascular permeability in the skin, as shown schematically in FIG. 1.

My discovery of this causal connection results from my deduction that the factors which I have observed to be involved in the onset or exacerbation of rosacea and the symptoms which are associated with rosacea can both be tied to the activation of bradykinin in the skin.

For example, the following conditions are known to exacerbate symptoms of rosacea: sun exposure, hot weather, bathing in hot water, high humidity, sweating, exercise, emotional stress, and spicy food. All of these factors increase bradykinin production in the skin, for example, via a heat associated activation of kallikreins, as shown in FIG. 1. Both kallikreins and bradykinins have been demonstrated to be activated following heat exposure. Tissue kallikreins play a particularly significant role in such kallikrein activation in the skin following a heat, exercise, or adrenergic related stimulus, given their colocalization with the bradykinin precursor kininogen in sweat glands (see, e.g., Regoli et al., Pharmacological Reviews 32: 1980; Bhoola et al., Pharmacological Reviews 44: 1992; Starr and West, Br. J. Pharmac. Chemother. 31: 178–87, 1967). Without wishing to be bound by any particular theory, I believe that the sun-induced activation of the bradykinin pathway is also caused, at least in part, by the UV component of sunlight.

In addition to the above factors associated with rosacea, I have observed that the symptoms of rosacea are also caused by conditions associated with high levels of angiotensin II. Included within these conditions is high renin essential hypertension, and especially secondary hypertension due to renovascular disease. As shown in the schematic of my discovery in FIG. 1, these forms of hypertension cause an increase in bradykinin production through the following steps: 1) renin is produced by the kidney in supranormal amounts; 2) renin stimulates an increase in angiotensin I; 3) angiotensin I is converted to angiotensin II by angiotensin converting enzyme (ACE); 4) angiotensin II causes an AT2 receptor-mediated increase in bradykinin, especially in the vasculature of the face and possibly other areas of the skin (Siragy and Carey, Hypertension 33: 1237–1242, 1999).

Turning to the second step of the analysis of my discovery, an increase in bradykinin in the skin can also be traced to the manifestation of many symptoms of rosacea. As further shown in the schematic in FIG. 1, increased bradykinin in the skin causes the symptoms of rosacea through inducing vascular changes (causing the symptoms of flushing, edema, vasodilation, erythema, and telangiectasia), inducing abnormal sensations in the skin (causing feelings of pain, burning, itching, and skin tightness), and chronic inflammation (causing fibroplasia, hyperplasia, papules, and pustules).

Bradykinin mediates these effects as follows. The increase in bradykinin causes vasodilation, increased vascular permeability, and a cytokine-induced migration of inflammatory cells, including mast cells, basophils, monocytes, macrophages, and leukocytes, to the site. The inflammatory cells in turn release prostaglandins, oxygen free radicals, and nitric oxide at the site, causing damage to the skin tissue, pain, and further vasodilation.

Inflammatory cells also release extracellular proteases, such as procollagenase, elastase, and cathepsin G. Once activated (for example, procollagenase is cleaved to form the active collagenase), these proteases degrade the connective tissue network, especially when their presence is not counterbalanced by antiproteases, such as the tissue inhibitors of metalloproteinases (TIMPs). The effect of procollagenase released by inflammatory cells is potentiated if kallikreins are concurrently activated at the site because kallikreins recognize procollagenase as a substrate and convert it to collagenase. As a result of chronic inflammation caused by repetitive bradykinin activation, changes in the functional properties of the connective tissue matrix induce skin coarseness and tissue fibrosis.

In summary, the treatment of the present invention is based on my development, elaborated herein, of the causal relationship between the activation of the bradykinin pathway and the development of symptoms of rosacea. Activation of this pathway causes these symptoms through inflammation-related changes in the skin, such as increased inflammatory cell infiltration, increased oxygen free radicals, increased nitric oxide, and increased matrix metalloproteases, as well as through vascular changes, such as vasodilation and increased vascular permeability. Given this causal relationship between the activation of the bradykinin pathway and symptoms of rosacea, an inhibitor of the bradykinin activation pathway provides effective therapy to treat or prevent symptoms of rosacea. Such treatment could be especially therapeutic where bradykinin is activated by external factors such as sunlight, heat and humidity, by the effect of exercise or sweating, or by internal factors such as elevated levels of angiotensin II. Similarly, such treatment should be particularly effective if symptoms of rosacea are caused by an elevated level of kallikrein in the skin or an increase in number or sensitivity of angiotensin AT2 receptors or skin bradykinin receptors, particularly B2 receptors.

Inhibiting the Bradykinin Activation-Related Pathway: Treatment for Rosacea

The present invention provides a method of treating or preventing rosacea in a patient by administering a compound that inhibits the bradykinin activation pathway in the skin. In this regard, an inhibitor of the bradykinin pathway includes those agents that reduce the effect of a component of the pathway, for example, a tissue kallikrein, plasma kallikrein, angiotensin II, a bradykinin, or an enzyme involved in arachidonic acid metabolism (for example, a nonsteroidal anti-inflammatory drug (NSAID)), by inhibiting or antagonizing the enzymatic activity of the component or by reducing the protein level of the component. This inhibition results in a reduction of the inflammation, vasodilation, or vascular permeability, or other bradykinin activation pathway-related changes in the skin.

Ideally, the inhibitor used is an inhibitor of bradykinin activity and is administered topically. Given that bradykinin is an autocoid that acts only locally, topical administration may be used to achieve a therapeutic dose in the skin to inhibit the pathological action of bradykinin without increasing the systemic concentration to a level that would cause adverse systemic side effects. If a kallikrein inhibitor is used for treatment, a tissue kallikrein inhibitor is preferred. Inhibition of a tissue kallikrein is predicted to be particularly effective in the treatment or prevention of rosacea, given that tissue kallikrein is released following thermal stimulation and is colocalized with the bradykinin precursor, kininogen (see, e.g., Regoli et al., Pharmacological Reviews 32: 1980; Bhoola et al., Pharmacological Reviews 44: 1992).

The treatment contemplates the use of one, or more than one, inhibitor. If multiple inhibitors are used, they can be directed against one or more pathway components. This inhibition of multiple components of the bradykinin activation pathway has the advantage of producing an additive or potentiated therapeutic effect, and, could include, for example, a treatment using both a kallikrein inhibitor and a bradykinin inhibitor. The inhibitory effect of a compound can be assessed, for example, by measuring the activity or level of a component of the bradykinin activation pathway in the skin, by assessing the appearance or degree of a symptom of rosacea, or by measuring a bradykinin activation pathway-related change in the skin, for example, inflammation, inflammatory cell infiltration, oxygen free radicals, nitric oxide, MMPs, vasodilation, or vascular permeability.

Ideally, the inhibitor does not completely inhibit the bradykinin activation pathway, but, rather, partially inhibits the pathway to reduce or eliminate the adverse effects related to rosacea without affecting other normal bradykinin actions. Such a result can be achieved through studies of dose response. For example, a series of doses of a kallikrein inhibitor, an angiotensin II AT2 inhibitor, a bradykinin inhibitor, and/or an NSAID, can be administered to determine which dose most effectively inhibits the symptom of rosacea, without causing significant undesirable side effects.

Techniques to Assess the Effectiveness of a Bradykinin Activation Pathway Inhibitor A compound that is known to inhibit a component of the bradykinin activation pathway, for example, a known inhibitor of kallikrein activity, angiotensin II AT2 activity, bradykinin activity, or a nonsteroidal anti-inflammatory drug (NSAID), can be assessed for its ability to treat or prevent symptoms of rosacea by testing the compound on a patient with a symptom of rosacea. The effectiveness can be quantitated, for example, using the Duluth Rosacea Scoring Instrument (Bamford et al., Arch. Dermatol. 135: 659–663, 1999). Alternatively, the compound can be tested to determine whether it exerts a physiologically relevant effect in biological assays. A compound can be administered to assess whether it can prevent or reverse a bradykinin activation pathway-mediated effect. In the case where heat, exercise, or angiotensin II produces a bradykinin activation pathway-related change in the skin, a compound that is an effective inhibitor is one that changes this value back towards the value observed in nontreated skin in a statistically significant manner. Examples of such assays are provided below.

Inhibiting a Component of the Bradykinin Activation Pathway

The effectiveness of a kallikrein inhibitor, an angiotensin II AT2 inhibitor, a bradykinin inhibitor, or an NSAID, as treatment for rosacea can be assessed by measuring whether the compound inhibits, the formation in the skin of bradykinin or downstream arachidonic acid products such as prostaglandins, leukotrienes, or thromboxanes in the skin. This reduced activity may result from inhibiting or antagonizing the specific activity of the targeted enzyme or autocoid, or from reducing its protein level in the skin.

Measures of bradykinin are tested on isolated skin samples according to well accepted methods for bradykinin and related kinins (Trautschold, Handbook of Expt. Pharmacol. Vol. 25, Springer-Verlag, 52–81, 1970; U.S. Pat. No. 4,801,613; U.S. Pat. No. 5,578,601).

Measures of the levels of arachidonic acid products can be conducted as previously described (Trautschold, supra; Vane, Nature New Biol. 231: 232–235, 1971; Vane, Inhibitors of prostaglandins, prostacyclin, and thromboxane synthesis. In Advances in Prostaglandin and Thromboxane Research, vol. 4, ed. Coceanu and Olley, Raven Press, New York, 27–44, 1978).

Assay for Matrix Metalloprotease (MMP) Induction

To assess the effectiveness of a bradykinin activation pathway inhibitor, collagenase, 92K gelatinase, or stromelysin levels are studied to determine whether the compound reduces the mRNA, protein expression, or total enzymatic activity of these MMPs.

To measure mRNA levels, skin samples are snap-frozen, and total RNA is isolated and analyzed for collagenase, 92K gelatinase, or stromelysin by northern blot using appropriate probes (Sato et al., Oncogene 8: 395–405, 1987; Fisher et al., J. Invest. Dermat. 96: 699–707, 1991; Angel and Karin, Matrix Suppl. 1: 156–164, 1992; Quinoncs et al., Biochem J. 302, 471–477, 1994; and Fisher et al., J. Invest. Dermatol. 105: 80–86, 1995). Frozen skin sections (5 micron) are mounted, fixed, treated, and hybridized as described in Fisher et al., J. Invest. Dermatol. 105: 80–86, 1995.

To assay for levels of protein in the skin, supernatant from skin samples homogenized, for example, in 20 mM Tris-HCl, pH 7.6, 5 mM CaCl2, and centrifuged at 3,000×g for 10 min, can be subjected to PAGE-SDS electrophoresis, and protein levels are assessed by western blot. Immunologic analysis of collagenase, gelatinase, and stromelysin is performed, for example, as described in Griffiths et al., N. Engl. J. Med. 329: 530–535, 1993.

Activity levels can be assessed by measuring hydrolysis of tritium-labeled fibrillar collagen (Hu et al., Analyt. Biochem. 88: 638–643, 1978), or gelatin zymography (Hibbs et al., J. Biol. Chem. 260: 2493–2500, 1985).

Compounds

Compounds that can be used for the treatment or prevention of rosacea inhibit a kallikrein, angiotensin II activation of the AT2 receptor, a bradykinin, or the arachidonic acid metabolic pathway. Kallikrein, angiotensin II, or bradykinin inhibitors may act by directly inhibiting or antagonizing the kallikrein, angiotensin II, or bradykinin pharmacological effect, by reducing their respective production or release, or by enhancing the activity of endogenous peptides that degrade a kallikrein, angiotensin II, or bradykinin. Inhibitors of the arachidonic acid metabolic pathway, such as NSAIDs, may act by inhibiting the enzymatic activity of an enzyme in the pathway, for example, cyclooxygenase, prostaglandin synthetase, or lipoxygenase, or by reducing the level of the enzyme in the skin. Examples of all such compounds are included below.

Kallikrein Inhibitors

Kallikrein inhibitors that can be used in the treatment or prevention of rosacea inhibit or antagonize the kallikrein enzymatic activity or reduce the kallikrein level in the skin. Kallikrein inhibitors include, but are not limited to, serpin, C1 inhibitor, α2 macroglobulin, antithrombin-III, ecotin, broad spectrum Kunitz-type serine protease inhibitors, such as aprotinin, and its variants (U.S. Pat. No. 5,786,328; U.S. Pat. No. 5,770,568), diisopropylfluorophosphate, and pefablock (Interchim).

A key issue in the preferred choice of a kallikrein inhibitor is specificity. The serine protease progenitor of kallikrein also gives rise to other serine proteases, and kallikrein shares many enzymatic features with other proteases. Examples of preferred kallikrein inhibitors that are specific for tissue kallikrein include substrate analog inhibitors of kallikrein, which correspond to the amino acid sequence of kininogen. These peptides have an amino acid sequence comprising positions 388 to 390 of kininogen and prevent the kallikrein cleavage of kininogen (U.S. Pat. No. 5,464,820).

Kallikrein antibodies can also be used.

Angiotensin Inhibitors

Angiotensin II inhibitors either inhibit or antagonize the angiotensin hormonal activity or reduce the level of angiotensin II in the skin such that activation of the AT2 receptor is reduced. Preferred inhibitors are either specific for the AT2 receptor, such as PD 123319 (Siragy and Carey, supra), or are balanced antagonists which block both the AT1 and AT2 receptors.

Bradykinin Inhibitors

The bradykinin inhibitors that can be used to practice the present invention inhibit or antagonize the bradykinin autocoid activity or reduce the bradykinin level in the skin. The inhibitors include, but are not limited to, CP0597 (Cortech) and the exemplary inhibitors listed in U.S. Pat. No. 5,700,779; U.S. Pat. No. 5,750,506; U.S. Pat. No. 5,610,140; U.S. Pat. No. 5,863,899, U.S. Pat. No. 5,849,863; U.S. Pat. No. 5,843,900; U.S. Pat. No. 5,834,431, U.S. Pat. No. 5,635,593; U.S. Pat. No. 5,416,191; U.S. Pat. No. 5,620,958; U.S. Pat. No. 5,563,162; U.S. Pat. No. 5,750,669; U.S. Pat. No. 5,574,042; WO 96/13485; WO 96/40639; WO 97/07115; WO 97/11069; EP 773,932 A1; EP 596,406 A1; EP 596,406 B1; EP 787,131 A1; EP 861,243 A1; EP 807,105 A1; EP 622,361 A1; WO 96/40639; WO 97/07115; WO 97/11069; EP 773,932 A1; EP 596,406 A1; EP 596,406 B1; EP 787,131 A1; EP 861,243 A1; EP 807,105 A1; EP 622,361 A1; and the indirect bradykinin inhibitors listed in U.S. Pat. No. 4,801,613. Preferred inhibitors are specific for the BK2 receptor, such as CP0597. Specifically excluded are icatibant and the compounds listed in U.S. Pat. No. 5,849,312; U.S. Pat. No. 5,212,182; EP 578,521; EP 564,972; EP 548,825; EP 552,106; FR 2,686,343; and WO 93/11789.

Other bradykinin inhibitors that can be used include the modified peptide analogs disclosed in U.S. Pat. No. 4,801,613, the nonpeptide antagonists disclosed in U.S. Pat. No. 5,578,601, and the peptide antagonists disclosed in U.S. Pat. No. 4,693,993.

Indirect bradykinin inhibitors which can be used inhibit one or more of the biological activities of bradykinin, and include antihistamines, bradykinin antibodies, benzodiazepine derivatives, high molecular weight ethylene oxide polymers, gallic acid esters, and serotonin inhibitors (U.S. Pat. No. 4,801,613).

Arachidonic Acid Metabolic Pathway Inhibitors

Any known compound that acts as a nonsteroidal anti-inflammatory drug (NSAID) including, but not limited to, salicylates and cyclooxygenase inhibitors can be used. Examples of some well established NSAIDs include naproxen, nabumetone, diclofenac, sulindac, oxaprosin, diflunisal, bromfenac, aspirin, piroxicam, indomethacin, etodolac, ibuprofen, fenoprofen, flurbiprofen, ketorolac, nimesulide, NS-398, and ketoprofen. Salicylates include aspirin, trisalicylates, acetominophen, oxaprosin, and salsalate. Examples of more modern NSAIDs are the cyclooxygenase inhibitors rofecoxib and celecoxib. All the above chemicals are commercially available from Cayman Chemical Co., Ann Arbor, Mich.; Sigma Chemical Co., St. Louis, Mo.; Proctor and Gamble, Cincinnati, Ohio; G.D. Searle Pharmaceuticals, Chicago, Ill.; and 3M Pharmaceuticals, St. Paul, Minn.

Formulations and Routes of Administration

Compounds can be administered systemically or topically, in an amount sufficient to prevent or treat symptoms of rosacea and may be administered by any appropriate route. For example, systemic administration may be parenteral, intravenous, intra-arterial, subcutaneous, intramuscular, intraperitoneal, intranasal, by aerosol, suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

For topical administration, the compounds will normally be formulated as creams, gels, ointments, sprays, or lotions. Conventional pharmacologically and cosmetically acceptable vehicles may be used. The compounds may also be administered in liposomal formulations that allow compounds to enter the skin. Such liposomal formulations are described, for example, in U.S. Pat. No. 5,169,637; U.S. Pat. No. 5,000,958; U.S. Pat. No. 5,049,388; U.S. Pat. No. 4,975,282; U.S. Pat. No. 5,194,266; U.S. Pat. No. 5,023,087; U.S. Pat. No. 5,688,525; U.S. Pat. No. 5,874,104; U.S. Pat. No. 5,409,704; U.S. Pat. No. 5,552,155; U.S. Pat. No. 5,356,633; U.S. Pat. No. 5,032,582; U.S. Pat. No. 4,994,213; and WO 96;40061. Examples of other appropriate vehicles are described in U.S. Pat. No. 4,877,805 and EPA Pub. No. 0586106A1.

The topical formulations may also contain additives such as emollients, skin permeation enhancers, pigments, and perfumes. In addition, the formulation may contain ingredients such as absorbent particles (e.g., polymer beads) that provide sustained release of the inhibitors to the skin. The weight concentration of inhibitor(s) in the formulation will usually be 0.01% to 10%, more usually 0.1% to 1%. Normally, about 50 mg of formulation will be applied per $cm^2$ of skin.

The inhibitors, whether delivered topically or systemically, are preferably administered prior to exposure to sunlight, or prior to the occurrence of any other condition known to exacerbate symptoms of rosacea. The application regimen (i.e. daily, weekly, etc.) will primarily depend upon the longevity (e.g. metabolism, half-life in the skin) of the inhibitor(s) and the molecular targets of their action. For topical administration, the regimen may also be affected by bathing, perspiration, and the extent of sunlight exposure. Usually, the formulation will be administered daily.

As indicated above, one or more inhibitors may be present in a given formulation. Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound will vary depending upon a number of factors, including the dosage of the drug to be administered, and the route of administration.

The formulations can be administered to human patients in therapeutically effective amounts (e.g., amounts which prevent, eliminate, or reduce the symptoms of rosacea) to provide therapy for the disorders described above. The preferred dosage of drug to be administered is likely to depend on such variables as the overall health status of the particular patient, the formulation of the compound excipients, and its route of administration.

OTHER EMBODIMENTS

All publications and patent applications mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art. Other embodiments are within the claims.

What is claimed is:

1. A method of treating rosacea, said method comprising administering to a patient a compound that inhibits angiotensin II activation of the AT2 receptor, said administering in an amount sufficient to reduce one or more symptoms of rosacea.

2. The method of claim 1, wherein said compound inhibits a symptom of rosacea comprising any of the following symptoms appearing in or associated with the skin: flushing, erythema, vasodilation, telangiectasia, edema, papules, pustules, hyperplasia, fibroplasia, itching, burning, pain, and skin tightness.

3. The method of claim 1, wherein said symptom is caused by inflammation, vasodilation, or increased vascular permeability in the skin.

4. The method of claim 1, wherein said compound blocks the AT2 receptor.

5. The method of claim 4, wherein said compound is PD 123,319.

6. The method of claim 1, wherein said administration is systemic.

7. The method of claim 1, wherein said administration is topical.

8. The method of claim 1, wherein said compound is in a liposomal formulation.

9. The method of claim 1, wherein said patient has elevated levels of angiotensin II.

* * * * *

UNITED STATES PATENT AND TRADEMARK OFFICE
CERTIFICATE OF CORRECTION

PATENT NO. : 7,105,172 B1 Page 1 of 1
APPLICATION NO. : 09/715644
DATED : September 12, 2006
INVENTOR(S) : John D. Bolla It is certified that error appears in the above-identified patent and that said Letters Patent is hereby corrected as shown below:

Column 1, Line 45, replace "lamina proprira" with --lamina propria--.

Column 8, Line 9, replace "inhibits," with --inhibits--.

Signed and Sealed this

Eleventh Day of December, 2007

JON W. DUDAS
*Director of the United States Patent and Trademark Office*